(12) United States Patent
Leung

(10) Patent No.: US 10,506,954 B2
(45) Date of Patent: Dec. 17, 2019

(54) MOBILE AUTOMATED HEALTH SENSING SYSTEM, METHOD AND DEVICE

(71) Applicant: eNano Health Limited, Pak Shek Kok (HK)

(72) Inventor: Patrick Shau-park Leung, Arcadia, CA (US)

( * ) Notice: Subject to any disclaimer, the term of this patent is extended or adjusted under 35 U.S.C. 154(b) by 0 days.

(21) Appl. No.: 15/056,163

(22) Filed: Feb. 29, 2016

(65) Prior Publication Data
US 2017/0245789 A1     Aug. 31, 2017

(51) Int. Cl.
| | |
|---|---|
| *A61B 5/145* | (2006.01) |
| *A61B 10/00* | (2006.01) |
| *C12Q 1/54* | (2006.01) |
| *G01N 21/78* | (2006.01) |
| *G06F 19/00* | (2018.01) |
| *A61B 5/00* | (2006.01) |
| *A61B 5/1477* | (2006.01) |
| *G16H 10/40* | (2018.01) |
| *G01N 21/80* | (2006.01) |
| *G01N 21/77* | (2006.01) |

(52) U.S. Cl.
CPC ........ *A61B 5/14532* (2013.01); *A61B 5/1477* (2013.01); *A61B 5/14507* (2013.01); *A61B 5/6898* (2013.01); *A61B 10/0051* (2013.01); *C12Q 1/54* (2013.01); *G01N 21/78* (2013.01); *G06F 19/324* (2013.01); *G16H 10/40* (2018.01); *A61B 2562/08* (2013.01); *C12Y 101/03004* (2013.01); *C12Y 111/01* (2013.01); *G01N 21/80* (2013.01); *G01N 2021/7759* (2013.01); *G01N 2201/0221* (2013.01); *G01N 2333/904* (2013.01); *G01N 2333/908* (2013.01)

(58) Field of Classification Search
CPC ............ A61B 5/14532; A61B 10/0051; G06F 19/366; G06F 19/324; G01N 21/78; G01N 2333/904; G01N 2333/908; C12Q 1/54; C12Y 111/01; C12Y 101/03004
See application file for complete search history.

(56) References Cited

U.S. PATENT DOCUMENTS

| | | | |
|---|---|---|---|
| 2014/0296089 A1* | 10/2014 | Holmes | G01N 35/026 506/9 |
| 2015/0359458 A1* | 12/2015 | Erickson | G01N 33/52 455/557 |

OTHER PUBLICATIONS

University of Cambridge. "Pocket diagnosis: App turns any smartphone into a portable medical diagnostic device." ScienceDaily. ScienceDaily, Mar. 19, 2014. www.sciencedaily.com/releases/2014/03/140319103612.htm (Year: 2014).*

* cited by examiner

*Primary Examiner* — Dennis White
(74) *Attorney, Agent, or Firm* — Bioinnovation Legal PLLC; James Christopher Schroeder

(57) ABSTRACT

The claimed invention relates to mobile computing monitoring of health statistics using chemically synthesized conjugate markers providing highly specific details of personal health states. Using portable computing and communications devices, commonly known as 'smartphones', personal health and wellness information is gathered from chemical markers and reported to the user. Chemical markers include chemicals which undergo a measurable color change when combined with body fluids such as saliva. Health information derived from chemical markers may be optically collected, locally reported and widely broadcast over a 'cloud based' internet data distribution system.

3 Claims, 3 Drawing Sheets

101    103      105    107    109

101  103         105  107  109

MOBILE AUTOMATED HEALTH SENSING SYSTEM, METHOD AND DEVICE

BACKGROUND OF THE INVENTION

Consumers are presently offered a wide array of smailphone based wellness platforms. Personal preferences based upon phone operating system, device color, design and shape are currently addressed by multiple market entrants.

One wellness smailphone system currently known as 'Fitbit' offers wearable bands in a variety of colors. Health tracking features are similarly anticipated on the 'iWatch' line of wearable computing devices.

Despite the numerous attempts for smailphone wellness market participants to differentiate, the actual health parameters measured are nearly indistinguishable. Heart rate monitors measure heart rate, accelerometers are used to derive activity and more robust models may even detect temperature or weight measurements.

The subject of the various devices, the human body, is a vastly complex system. Even if a wrist band sensor is sensitive enough to detect heart rate and activity it is still just a pressure and motion sensor. Despite tremendous gains in computing power and communication ability, existing 'wellness' devices on the market today do not provide accurate or meaningful wellness knowledge to their users.

SUMMARY OF THE INVENTION

Unlike general purpose health and wellness consumer applications, the presently claimed invention leverages mobile computing platforms in both localized and cloud computing embodiments together with breakthroughs in chemistry marker based technology. Personal wellness applications are greatly enhanced through acquisition and reporting of high value health and wellness data obtained through non-invasive means.

In specific embodiments of the claimed invention, chemical sensors include one or more labeling compounds which can be visibly identified and interpreted by the corresponding mobile communications device and related system. In a preferred embodiment, the system includes an in vitro diagnostic device which uses reagents for both qualitative and quantitative analysis of salivary glucose. A preferred embodiment sample collection device is composed of a plastic cassette with a test strip, which is responsible for the salivary glucose testing. The presence of glucose in salivary induces a color change, from colorless to red, in a test strip. pH dye is used to detect the pH of the saliva. Color changes depending on the pH of the saliva and glucose changes from white to pink.

Chemical sensors enable non-invasive testing to obtain valuable biological information. Currently, the vast majority of diabetic patients must undergo invasive and painful blood sampling to determine baseline blood glucose level monitoring. In one illustrative aspect of the invention, a chemical indicator capable of indicating glucose levels is embedded in a disposable substrate and placed in sample collection housing. The detection of salivary glucose is based on a coupling reaction between glucose oxidase and peroxidase. Glucose oxidase oxidizes the salivary glucose into gluconolactone and hydrogen peroxide (H2O2). In the presence of peroxidase, 10-acetyl-3,7-dihydroxyphenoxazine reacts with H2O2 in a 1:1 stoichiometry in order to produce a white to pink color. In a preferred embodiment, the chemical sensor is a compound having the following structural formula:

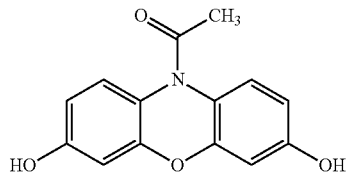 [SMILES: CC(=O)N1c2ccc(O)cc2Oc2cc(O)ccc21]

Traditional glucose sensing for diabetics would involve blood sample removal from the subject. In the present example, saliva is obtained by non-invasive means and used in place of a blood sample. Salivary glucose levels can be tested qualitatively by comparing visually the color of the test strip and the color blocks printed on the cassette. Alternatively, the salivary glucose can be quantified by capturing the image of the used cassette which is subsequently analyzed by software. Upon exposure to the chemical sensor in the disposable substrate and sample collection housing, visual readings are taken by a smailphone device and used to determine corresponding health and wellness information.

It is a present and intended consequence of the claimed invention that the chemical sensor/biological sample conjugate is obtained in a wide variety of physical vessels and provide positive sample results in a wide variety of ways which can be machine read. Using a disposable housing for biological sample capture is by way of illustration and not limitation. More substantial and robust chemical sensors and sample capture housings may be employed within the spirit and scope of the disclosed invention.

Health and wellness information obtained from chemical sensors may be machine read through a variety of means which include not only visual and fluorescent detection but also transmitted by near field communication techniques.

BRIEF DESCRIPTION OF THE DRAWINGS

The accompanying drawings are included to better illustrate exemplary embodiments of the claimed invention.

DETAILED DESCRIPTION OF THE INVENTION

Figure 1:
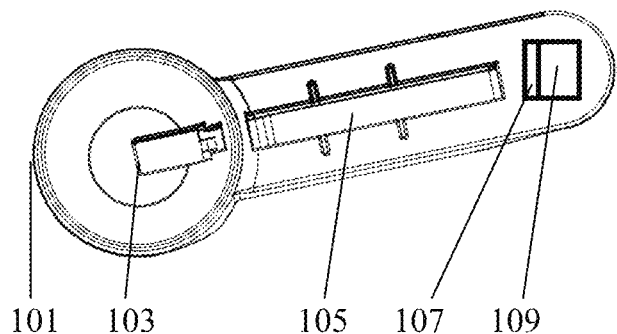
FIG. 1 shows an illustrative embodiment of a health sample collection device with sample collection housing and one or more chemical sensors and positive sample reporting means embedded within a matrix.

FIG. 1 shows health sample collection device (101) with sample collection housing (103) and one or more chemical sensors including (not shown) and positive sample reporting means (not shown) embedded within a disposable matrix (105). In the illustrative example, smailphone enabled wellness information capture is aided through optical data standardization bar (107) and unique sample collection device identifier (109).

Figure 2:
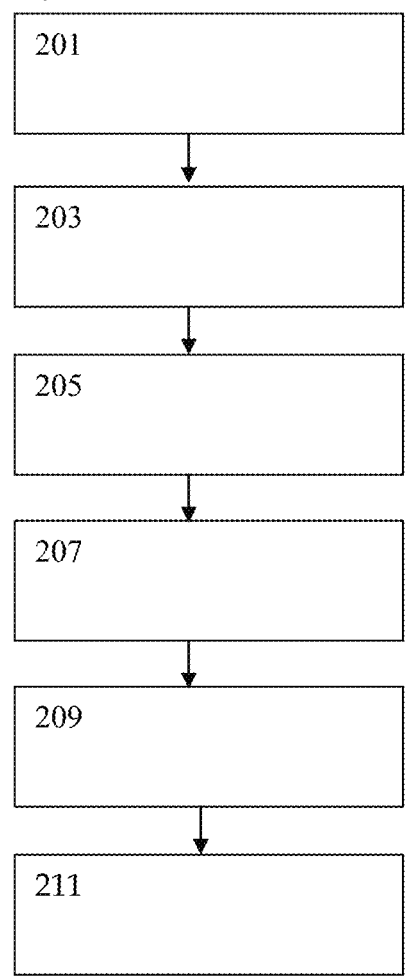
FIG. 2 is a flow diagram of illustrative health information data capture method according to the claimed invention.

FIG. 2 is a flow diagram of illustrative health information data capture method according to the claimed invention. Sample capture step (201) exposes sample (not shown) to health sample collection device (not shown) and begins exposure time calculation on smailphone (not shown). Depending upon the particular health sample under analysis, exposure time may be a critical step in determining accurate health measurements.

After sample capture step (201) results in the appropriate exposure time as determined by the smailphone (not shown), results photo capture step (203) takes place with one or more photos taken of the health sample collection device (not shown) incorporating the chemical based sensors with reporting indicators (not shown).

Color determination step (205) normalizes sample results (not shown) against optical data standardization bar (not shown) on the health sample collection device (not shown). During color determination step (205) color based results are normalized to yield standardized results regardless of mobile device camera or brand utilized. Results may be further optimized through background removal step (207) where background noise is removed.

Results association step (209) reads the QR code (not shown) on health sample collection device (not shown) and links data from sample capture to an individual health and wellness profile. User privacy is maintained as a direct and intended consequence of the illustrative example. Should a health sample collection device be misplaced or stolen, user identity cannot be determined solely by physical examination of a particular device.

Results interpretation step (211) matches chemical sensor display data (not shown) with a corresponding user and reports the results back on the smartphone device. Results interpretation may be derived from cloud based computing (not shown) or in the alternate on a particular smartphone device. As a result of the disclosed system and method, a novel and robust platform for personal health determination maintains privacy while allowing for specific results data sharing locally and over cloud based computing and telephony networks as desired.

Figure 3:
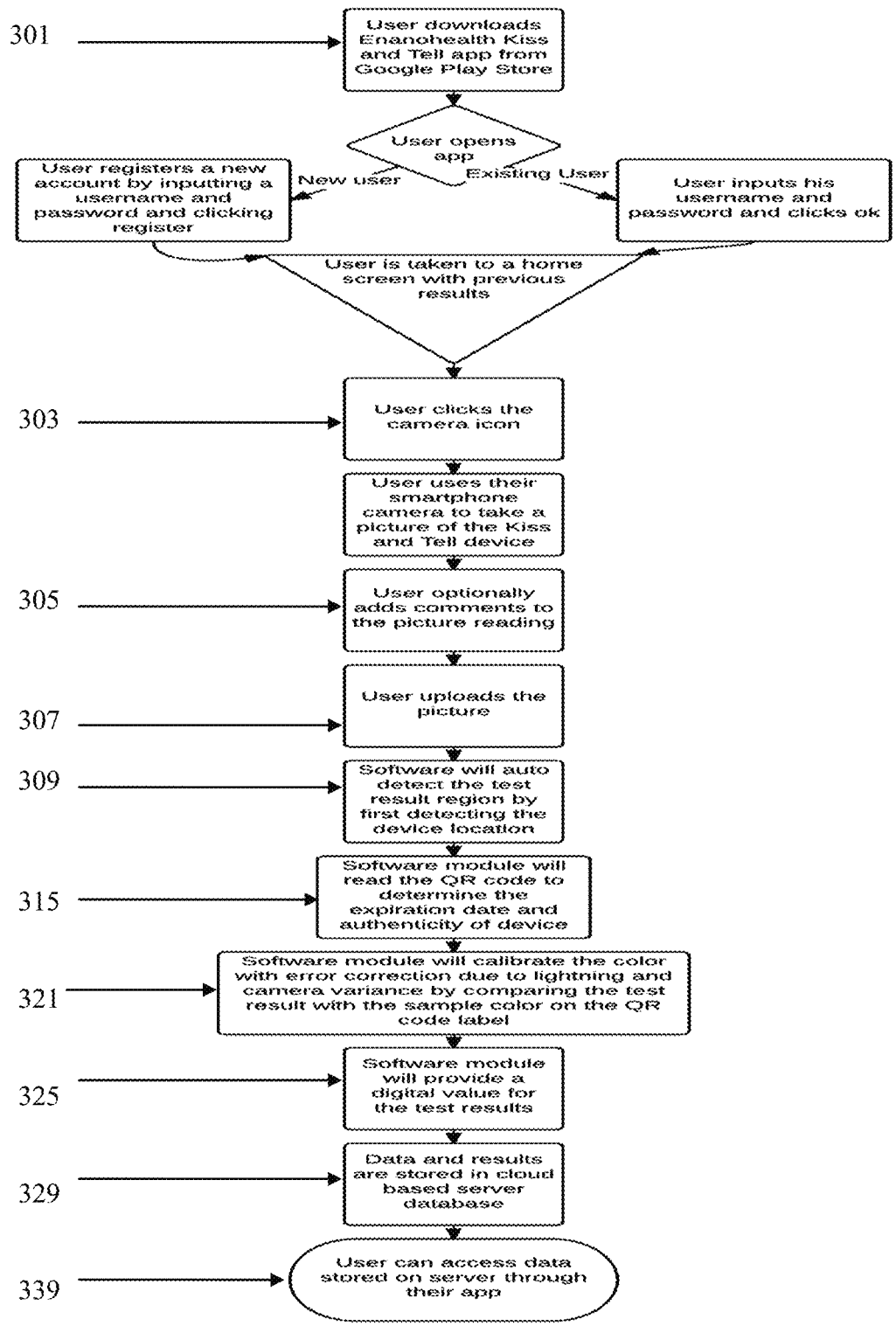
FIG. 3 is a flow diagram further illustrating health information data capture method according to the claimed invention.

FIG. 3 is an enhanced flow diagram of illustrative health information data capture method according to the claimed invention expanded to include device registration and data reporting feature sets. Device configuration step (301) downloads software to user smartphone (not shown) and if needed assigns user with a unique user id and password. Once logged in the user may be presented with previous results, comments and interpretation. Data capture step (303) begins with the user manually selecting the camera icon (not shown) within the application. Optional comment step (305) incorporates user comments into the specific data set getting captured.

Uploading step (307) uploads the captured picture (not shown) to the user smartphone (not shown) for results interpretation. Location identification step (309) takes place with smartphone software auto-detection of test result region through device location determination.

Authentication step (315) optically reads device QR code (not shown) using a software module to determine the expiration data and authenticity of device.

Error correction step (321) calibrates photo color with error correction to correct for lighting and camera variances by comparing the test result with the sample color bar on the QR code label.

Results reporting step (325) provides a digital value for the test results which may be graphically depicted on the user smartphone (not shown).

Results uploading step (329) transmits data, results and any optional comments to a cloud based server database (not shown).

User data access step (339) may take place on smartphone (not shown) to display data via the user application (not shown) taken from either cloud based or locally stored results.

Figure 4:
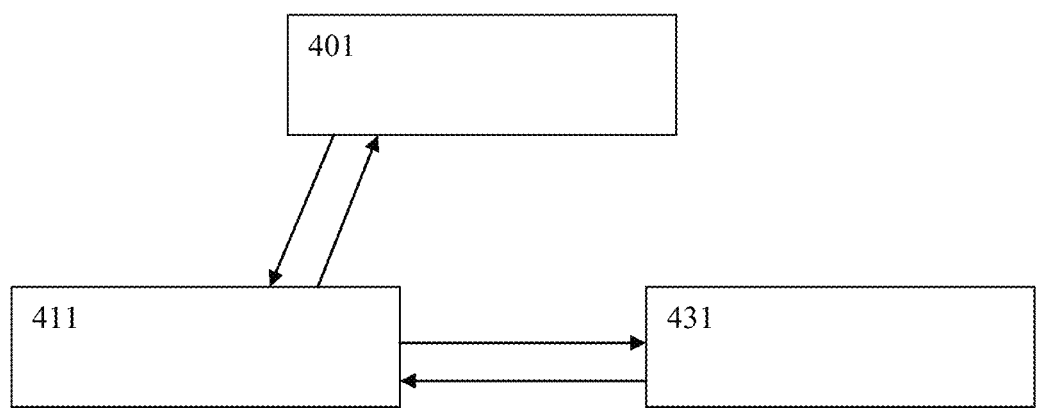
FIG. 4 is a schematic representation of the wellness system component elements.

FIG. 4 is a schematic representation of an illustrative example of the wellness system component elements. Health sample collection device (401) captures user samples (not shown) and chemical based sensors which are hybridized together.

In the presence of a positive sample, results are measurable by a computing device such as a smartphone (411). Results data capture may take place by optical measurement of smartphone (411) and in alternate foreseeable variants may also take place through near field communication wireless transmission. Smartphone (411) not only captures and transmits results but also displays results as well. While results may be locally interpreted, it is a direct and intended consequence of the illustrative example that results are uploaded to one or more cloud computing elements (431) for data interpretation and sharing.

Results provided by smartphone (411) may include specific wellness data such as glucose levels but also may include data history as well as correlation between data results and pharmaceutical requirements of the user. Alerts based upon missed pharmaceutical dosing may be alerted to the user by utilization of timing functions. Present and future dosing optimization may be provided based upon results interpretation. Near field communication readings may alert the user to the presence or absence of sufficient pharmaceutical dosing by reading RFID labels or tags (not shown) corresponding to proscribed pharmaceuticals in the immediate presence of the user.

Communications in the illustrative system may take place by each element including cloud (431) based, smartphone (411) based and health sample collection device (401) based. Cloud (431) based embodiments may not only send health results to smartphone (411) but also to health care medical providers (not shown) and friends and family (not shown). Smartphone (411) reporting may alert not only the user (not shown) but also provide automated audible and visual alerts in the case of an incapacitated user. In another alternate and foreseeable variant, health sample collection device (401) may provide immediate results feedback to the user (not shown) by way of physical means such as haptic feedback.

Illustrative examples are provided by way of illumination and not by way of limitation. Readily foreseeable variants include alternate embodiments including variants of physical location, number of units and alternate sensing, computing and communications means.

I claim:

1. A personal health monitoring system consisting of:
A personal communication smartphone device incorporating one or more central processing units configured to interpret glucose in saliva, one or more cameras, internet connection means and near field wireless communication means, cloud based data storage and computing resources programmed to detect glucose in saliva color change of detection chemicals of a sample detector health sample interpretation software programmed to detect glucose in saliva color change of the detection chemicals of an receptacle, health sample collection means and health sample detector wherein said health sample detector additionally comprises one or more health sample detection chemicals which in the presence of peroxidase, 10-acetyl-3,7-dihydroxyphenoxazine reacts with $H_2O_2$ in a 1:1 stoichiometry to produce a red color change in the presence of glucose in a saliva sample.

2. A personal health monitoring system consisting of:
A personal communication smartphone device incorporating one or more central processing units configured to interpret glucose in saliva, one or more cameras, internet connection means and near field wireless communication means,
cloud based data storage and computing resources programmed to detect glucose in saliva color change of said detection chemicals of a sample detector,
health sample interpretation software programmed to detect glucose in saliva color change of the detection chemicals of an receptacle, health sample collection means and health sample detector wherein said health sample detector is one or more health sample detection chemicals which in the presence of peroxidase, 10-acetyl-3,7-dihydroxyphenoxazine reacts with $H_2O_2$ in a 1:1 stoichiometry to produce a red color change in the presence of glucose in a saliva sample and has the following structural formula:

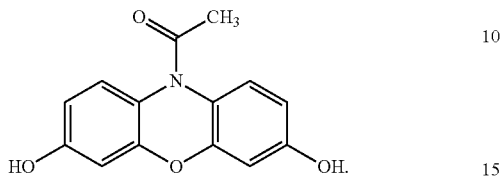

3. A method for personal health data collection consisting of the steps of:
  Exposing one or more chemical biosensors to a biological sample,
  Capturing data derived from the one or more chemical biosensor reporting based on biological sample exposure captured by user smartphone device configured to interpret measurable glucose in saliva wherein the one or more chemical biosensor is one or more health sample detection chemicals which in the presence of peroxidase, 10-acetyl-3,7-dihydroxyphenoxazine reacts with $H_2O_2$ in a 1:1 stoichiometry to produce a red color change in the presence of glucose in a saliva sample,
  Interpreting data captured from chemical biosensor, and
  Reporting health and wellness information derived from data captured from chemical biosensors.

* * * * *